United States Patent [19]
Rose

[11] Patent Number: 5,223,428
[45] Date of Patent: Jun. 29, 1993

[54] METHOD FOR IN VITRO CULTURE OF MAMMALIAN CELLS

[75] Inventor: Sam Rose, San Francisco, Calif.

[73] Assignee: Baxter International Inc., Deerfield, Ill.

[21] Appl. No.: 411,227

[22] Filed: Sep. 22, 1989

Related U.S. Application Data

[63] Continuation of Ser. No. 921,741, Oct. 22, 1986, abandoned, which is a continuation of Ser. No. 796,522, Nov. 8, 1985, abandoned, which is a continuation of Ser. No. 449,779, Dec. 14, 1982, abandoned.

[51] Int. Cl.$^5$ .................. C12N 5/06; C12P 21/00
[52] U.S. Cl. .................. 435/240.242; 435/70.1
[58] Field of Search .................. 435/240.241, 240.242, 435/240.25, 285, 286, 312, 313, 813, 818, 182, 244, 245, 70.1

[56] References Cited

U.S. PATENT DOCUMENTS 4,204,042  5/1988  Chelle .................. 435/314
4,537,860  8/1985  Tolbert et al. .................. 435/240.242

FOREIGN PATENT DOCUMENTS 0056761  7/1982  European Pat. Off. .................. 435/240.242

OTHER PUBLICATIONS

Rose, "Dual-Rotary Circumfusion System", Dr. Krise et al., Tissue Culture, Academic Press, 1973, 283–291.

Primary Examiner—David L. Lacey
Assistant Examiner—George C. Elliott
Attorney, Agent, or Firm—St. Onge Steward Johnston & Reens

[57] ABSTRACT

Cells producing a desired product or products, such as antibodies, are cultured with a culture medium comprising lymph. The lymph is continuously flowed across a semi-permeable membrane, on the other side of which are the cells to be cultured. The membrane is sized so as to retain cells, and their desired products, on one side of the membrane while permitting components of the lymph-containing culture medium (flowing across the other side of the membrane) to pass through the membrane to provide nutrition, etc. to the culturing cells.

6 Claims, 4 Drawing Sheets

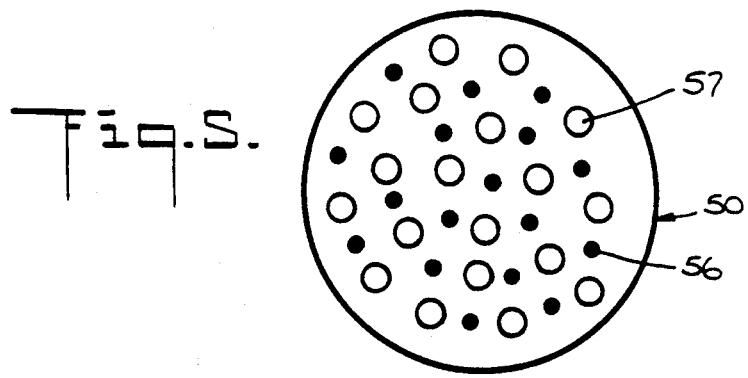
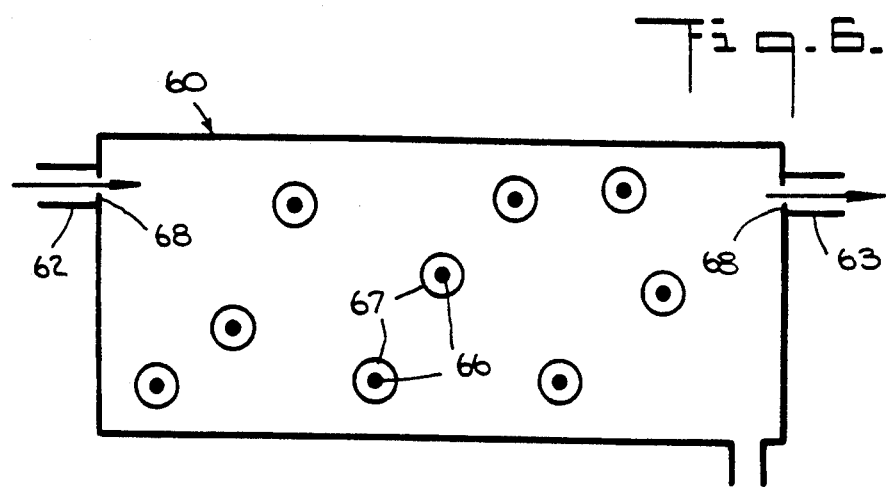
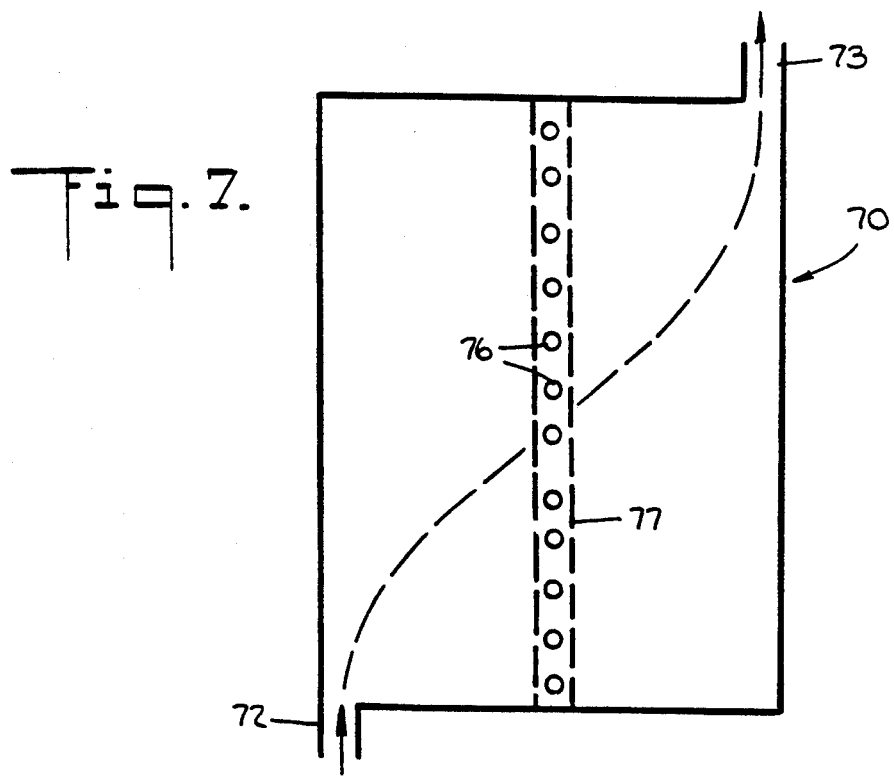

METHOD FOR IN VITRO CULTURE OF MAMMALIAN CELLS

This is a continuation of application Ser. No. 06/921,741, filed Oct. 22, 1986 and now abandoned; which is a continuation of application Ser. No. 06/796,522, filed Nov. 8, 1985 and now abandoned; which is a continuation of application Ser. No. 06/449,779, filed Dec. 14, 1982 and now abandoned.

BACKGROUND OF THE INVENTION

The present invention relates to a method for culturing living cells and, more particularly, to a method for economically culturing living cells in vitro in a manner which closely simulates the in vivo environment in which the living cells normally exist.

There is a large array of bio-medically useful products which are derived from mammalian systems. These products, arbitrarily classified according to their increasing size and molecular complexity, include (a) small molecules such as peptides (anti-diuretic hormone, oxytocin, antigenic portion of viral proteins); (b) intermediate molecules (insulin, interferon, lymphokines, growth hormone, thymus stimulating factor); (c) large complex molecules such as antibodies; and (d) whole organisms and cells (antibody producing cells, tumor cells, endothelial cells, vaccines).

Modern methods of manufacturing natural products include chemical synthesis, genetic engineering and mass cell culture. At the present time, chemical synthesis is not often used for it is only applicable to simple, small molecules such as peptides with 20 amino acids or less, and even as to these the process is very expensive. Genetic engineering is not applicable for making large complex molecules such as natural antibodies to be used for treatment and other purposes. Moreover, both with chemical synthesis and with genetic engineering, each new product is a major research and manufacturing endeavor and, hence, these methods are not easily applicable to making families of molecules such as antibodies or lymphokines.

In contrast, all natural products can, in principle, be produced by the mass culture of the very organisms or cells making such products. Once a suitable culture system has been established, moreover, it can be generally applied to all products produced by cells or organisms without the need for embarking upon a major research effort for each different product.

Despite these recognized advantages of mass culture as a potentially universal means for producing the large array of products obtainable from mammalian systems, the use thereof has not heretofore been practical, primarily for reasons of economics, i.e., the cost of culturing a given number of cells or organisms is extremely high.

The system in which cells or organisms are cultured in vitro theoretically is designed to provide an environment in which the cells or organisms can perform the essential functions (e.g., growth, product production, waste excretion) performed by the cells or organisms in vivo. In practice, however, the natural and/or synthetic culture media conventionally employed for this purpose are far from ideal in many respects and, more importantly, are extraordinarily expensive. In addition, known culture systems are not easily adapted to accommodate the large number of cells required to economically produce a sufficient quantity of a given product, and lack means for economically and efficiently removing from the system the desired products being made by the culturing cells.

One of the methods known for the in vitro culture of a large number of cells is "suspension culture", wherein a suspension of cells and culture medium is brought about and sustained by stirring or movement of the apparatus containing the cells and medium. Suspension culture is desirable since the environment around every cell is substantially the same and each cell can derive its nutrition from, and excrete its waste and products into, the medium surrounding the entire surface of the cell. However, the suspension culture processes practiced in the art, wherein culture medium is caused to flow in and out of an apparatus (culture chamber) containing the cell/culture suspension exhibit a number of substantial disadvantages, particularly with respect to the means, e.g., filters, employed for retaining the cells in the culture chamber while medium flows therethrough and the ability to collect from the system the desired products being made by the cells.

Apart from the disadvantages of typical suspension culture techniques, it is also known that some cells simply will not grow, or grow only poorly when in suspension. In these cases, it has been proposed to attach the cells to a surface or substrate thereby facilitating their ability to grow in standard tissue culture media. The substrate may be the surface of a culture chamber or vessel, micro-beads (see, e.g., M. Hirtzenstein, et al., "Microcarriers For Animal Culture: A Brief Review Of Theory And Practice", Proceedings Of The Third General Meeting Of The European Society For Animal Cell Technology (1979)) or the surface of hollow fibers (see, e.g., R. A. Knazek, "Cell Culture Of Artificial Capillaries: An Approach To Tissue Growth In Vitro", Science, 178, p. 65 (1972)).

Significant advances in the art of in vitro culture of cells are described in my U.S. Pat. Nos. 3,964,467 and 4,064,006 with respect both to the medium in which the cells are cultured and to apparatus which facilitate the mass culture of cells either in suspension or affixed to a surface. In particular, the foregoing patents describe the use of fresh flowing cell-free lymph as a culture medium for living cells. The cells are contacted with the flowing cell-free lymph in a suitable chamber in which the cells may exist either in a free state or bound to the surface of the vessel or to inert carrier particles. In one embodiment, the cell-free lymph and the cells to be cultured are contacted in a centrifuge which is periodically accelerated and decelerated to, respectively, hold the cells in a fixed position and then to disturb the cells from this fixed position and disperse them in fresh cell-free lymph.

As described in the aforementioned U.S. Patents, the procedure and apparatus developed for in vitro culture also makes possible an "in vivo - in vitro" culture method wherein the host is linked, by way of its lymph, to explant tissues or cells. Thus, a patient or subject is treated, by performing thereon a thoracic duct fistula (and optionally by raising the patient's capillary filtration flow) so as to assure that the tissue through which the lymph percolates does not significantly add or subtract molecules to or from the lymph. (See generally my U.S. Pat. Nos. 3,719,182 and 3,857,393 regarding this procedure). Lymph collected from the patient in this manner is treated so as to separate cells therefrom, and the cell-free lymph obtained in this manner is then utilized as the culture medium for living cells.

The processes described in the present invention represent important advances over my earlier culture methods, particularly with respect to the ability to provide an in vitro culture system wherein the cells are subjected to an environment which permits them to function in a manner closely simulating that encountered in vivo, permits the efficient removal of desired products from the cells being cultured and provides important advantages in the efficiency, economy and flexibility of operation.

SUMMARY OF THE INVENTION

In accordance with one aspect of the present invention, methods for the in vitro and in vivo - in vitro culture of living cells are provided wherein the cells are cultured with flowing lymph across a semi-permeable membrane sized so as, on the one hand, to prevent the cells from actually entering the flowing lymph stream while, on the other hand, permitting the cells to be bathed by the flowing lymph and to receive nutrition from the flowing lymph.

According to more particular aspects of the present invention, a number of methods are provided for arranging the cells within a suitable vessel or apparatus wherein the cells are contacted with flowing lymph across a semi-permeable membrane.

According to other features of the present invention, various means are provided for collecting desired products made by the cells during the culturing process.

In another aspect of the present invention, provision is made for the addition of particular materials to either the "cell-side" of the semi-permeable membrane or to the flowing lymph itself to achieve desirable advantages regarding, for example, the nutrition of the cells.

According to a further aspect of the present invention, a desired oxygen tension is maintained in the cells during the culturing either by direct addition of oxygen gas to the system or through use of oxygen-carrying and/or oxygen-liberating materials.

In yet another aspect of the present invention, involving the in vivo - in vitro culture of cells with lymph, methods are described for treating the living lymph source so as to increase its flow of lymph for use in the culture of cells according to this invention and/or to provide particular characteristics to the lymph which make it more advantageous for use as a culture medium.

These and additional features and embodiments of the present invention, and the advantages obtained therewith, are described in further detail in the following description, figures and examples.

As used herein, "cells" is intended to encompass mammalian and non-mammalian tissues and cells, micro-organisms and parasites.

BRIEF DESCRIPTION OF THE DRAWINGS

FIGS. 1 through 7 represent schematic views of apparatus useful in the methods of the present invention for arranging cells for culture with flowing lymph across a semi-permeable membrane.

DETAILED DESCRIPTION OF THE INVENTION

Figure 1:
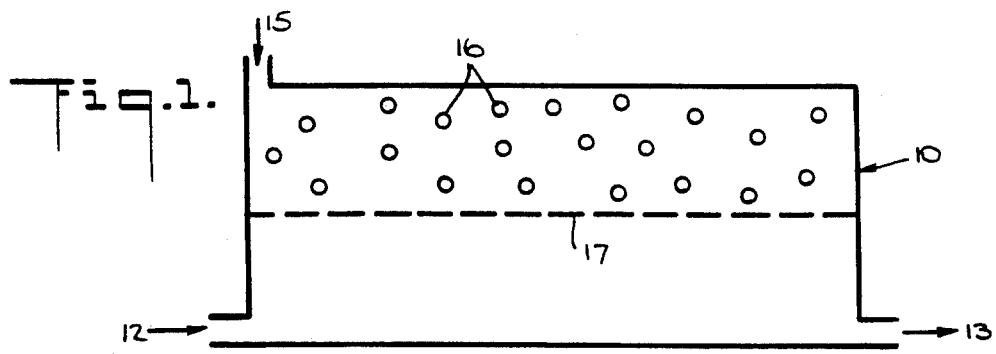

Primary features of the present invention involve the manner in which the cells and lymph are contacted, the manner in which desired products produced by the cells are removed from the system, the manner in which the cells are oxygenated during culturing and the manner in which the lymph culture medium is obtained from a living host and employed as a culture medium. The description which follows treats these various features under separate headings, but it will be apparent that numerous interactions between or among these features can occur or be intentionally arranged to occur such that the features are not per se independent. Where possible in the following description, discussion is made of any alterations of or effects on individual features which come about in those cases where more than one such feature is combined in an overall process, but it is not intended that such discussion delimit the scope of the many combinations of features possible according to the present invention.

OBTAINING OF LYMPH FOR USE AS A CULTURE MEDIUM

The source of lymph utilized as the culture medium (or as a component of the culture medium) according to the present invention may be any living mammal from which lymph can be obtained. No absolute limitation exists with respect to the need or desirability of utilizing lymph from a species of the same or similar type as the species from which the cells to be cultured are derived, but considerations of the general compatibility of the cells with the components of the lymph to which they will be exposed obviously may dictate preferred use of one mammal over another as the lymph source.

A preferred lymph source is a mammal from which a significant absolute quantity of lymph can be removed (e.g., continuously) without adversely affecting the health of the mammal, for example, a cow. While in certain instances it may be found that the mammal can survive either a continuous or periodic removal of a portion of its lymph, generally it is desirable to give replacement therapy to the mammal, for example, by return to the mammal of the lymph after its use as a culture medium (optionally with prior removal from the lymph of certain components) or by giving the mammal other suitable types of fluids or materials.

Removal of lymph from the mammal can be achieved by performing a thoracic duct fistula on the mammal. See, for example, my prior U.S. Pat. Nos. 3,719,182 and 3,857,393.

Choice of a particular mammal and/or alteration of the physiology of the mammal can be used to obtain certain advantages in the subsequent culturing using the lymph obtained from such mammals. For example, the absolute amount of lymph produced by a given mammal source can be substantially increased over normal levels by force feeding the animal (e.g., by high levels of intravenous fluid administration) so as to induce a large amount of lymph production. Still further, various means can be employed to produce lymph having desirably high albumin content and a low level of immunoglobulin. In yet another example, where the cells to be cultured by the lymph require the presence of certain molecules for their growth or for their production of particular products, it is possible to induce the animal to produce lymph containing these desired signal or helper molecules.

In the preferred practice of this invention, the lymph is continuously collected from the mammal and continuously utilized in a culture system (with optional continuous or periodic return of lymph or other replacement materials). However, lymph also may be collected from the mammal on a periodic basis and either utilized immediately in a culture system or stored for use at some later time. Even in a continuous system, it is not necessary that the rate of lymph removal from the mammal be tied to the rate at which the lymph is used as a culture medium since a variety of holding vessels may be employed in the process either to handle excess lymph production or to accumulate lymph until a desired quantity is obtained.

In all cases, the lymph is obtained from the mammal under conditions which insure the sterility of the lymph, i.e., which protect against the growth or presence therein of undesired materials which would be detrimental to the cells which will be cultured in the lymph.

CULTURING OF LIVING CELLS WITH LYMPH

The most basic requirement of the culturing method of the present invention per se is that the cells to be cultured not become commingled with cells in the lymph. This requirement can be met in two ways, i.e., either (1) the lymph is first rendered "cell-free" and then utilized in the culture of cells or (2) the "contacting" of the lymph and cells be done in a manner such that, notwithstanding the use of cell-containing lymph, the lymph cells per se do not mix with the culturing cells.

With respect to the former, the removal of cells from the lymph fluid can be accomplished in any manner which does not result either in damage to the resultant cell-free lymph fluid or significant loss of cell-free lymph fluid or desired components thereof. For example, centrifugation of the lymph obtained from the mammal is an effective means for obtaining cell free lymph. Cell-free lymph also may be obtained through the use of appropriately sized filters through which the lymph is passed to result in a cell-free permeate. Given the relatively large size of the cells, such filtration may easily be arranged so as to produce a permeate containing all but the cells of the original lymph. However, as discussed in further detail hereinafter, it may in certain cases be desirable to choose filters which not only render the lymph cell-free but also selectively remove particular compounds or classes of compounds from the lymph. Other techniques of separating cells from lymph may be employed such as packed columns and the like, although generally more care must be taken in such cases to insure that the columns do not become plugged, blocked or increasingly selective with time.

In the case where lymph which has not been made cell-free is employed as the "culture medium", it is necessary that the lymph be maintained separate from the culturing cells, i.e., the lymph and culturing cells are "contacted" in a manner which permits desired portions of the lymph to contact the cells but which prevents the lymph cells from achieving such contact. To this end, the lymph and culturing cells are contacted across a semi-permeable barrier sized so as to permit contact of the permeable portions of the lymph with the culturing cells while the lymph cells remain physically separated from the culturing cells. The membrane is also sized, of course, so as to prevent the culturing cells from crossing the barrier and commingling with the cell-containing lymph. As discussed in more detail hereinafter, the semi-permeable barrier can be chosen so as not only to retain cells in the lymph apart from the culturing cells, but also to permit only selected components of the lymph from contacting the culturing cells or prevent certain products from the culturing cells from crossing the barrier into the lymph.

The semi-permeable barrier may comprise a flat, sheet-like semi-permeable membrane or a hollow fiber or fibers made from semi-permeable material. In the latter instance, the cells to be cultured can be arranged to be either within or outside the fibers. In an alternative embodiment, the semi-permeable barrier constitutes the surface of a bead-like structure in which the cells are contained, a multiplicity of such beads being used to encapsulate the entire population of cells being cultured.

Whether cell-free or cell-containing lymph is employed as the culture medium, it is also possible to dilute the lymph to substantially less than its original or normal concentration of materials therein for use as a culture medium according to the present invention. By way of example, the originally obtained lymph may be diluted with salt solutions, amino acids, sugar, standard tissue culture medium or even blood or components thereof. In certain cases the dilution is for the purpose simply of rendering the lymph more easily flowable or for increasing the actual amount of culture medium. In other cases, however, dilution of the lymph with various solutions also serves the purpose of obtaining certain advantageous results in the culturing process per se, for example, by providing extra nutrition or oxygenation to the culturing cells.

The foregoing considerations are illustrated with reference to the following description and figures.

Referring to FIG. 1, a suitable apparatus 10 is employed having inlet port 12 and outlet port 13 for the entrance and exit, respectively, of lymph into and out of the apparatus. Cells 16 (culturing cells) are confined to a distinct portion of the apparatus by a semi-permeable flat, sheet membrane 17 having a pore size smaller than that of the culturing cells yet large enough to permit lymph or portions thereof or materials therein to come in contact with the culturing cells. An appropriate inlet/outlet port 15 is provided to supply and/or remove cells to or from the apparatus and/or, as described in more detail hereinafter, to supply particular materials to the "cell-side" of the membrane, i.e., the portion of the apparatus in which the culturing cells are confined.

In the apparatus of FIG. 1, the lymph may, as earlier noted, be so-called "intact" lymph (i.e., cell-containing) or cell-free lymph. Where the lymph is intact lymph, the use of membrane 17 is mandatory and the membrane must be sized, at a minimum, so as to prevent cells in the lymph from passing through the membrane and commingling with the culturing cells. Again as earlier noted, the membrane can also in such cases be sized so as not only to perform the foregoing function but also to selectively exclude particular lymph components (in addition to cells) from contacting the culturing cells. By way of example, the size (porosity) of the membrane can be chosen so as to exclude from the "lymph" actually contacting the culturing cells all components of the original lymph above about 100,000 molecular weight. Operation in this manner may be desirable where, for example, it is desired or required to prevent contact between culturing cells (or the products being made by culturing cells) and immunoglobulin or other high molecular weight materials.

Where the lymph employed in the process and apparatus of FIG. 1 is lymph which previously has been rendered cell-free, membrane 17 is not strictly required since there is no concern for the commingling of culturing cells and cells in the lymph. In the preferred practice of this invention, however, even cell-free lymph is contacted with the culturing cells across a semi-permeable membrane or barrier. The primary reasons for this are two-fold. In the first instance, where it is desired that certain components of the lymph not come in contact with the culturing cells, it has been found to be more efficient to achieve this exclusion after the lymph has been made cell-free rather than attempting to achieve this exclusion at the same time as the lymph is made cell-free. In other words, where, for example, it is desired that components of the lymph above 100,000 molecular weight not come into contact with the culturing cells, this condition can be accomplished either by (a) admitting cell-containing lymph to the culture vessel and choosing a semi-permeable barrier which not only prevents cells in the lymph from contacting the culturing cells but also resists permeation of components greater than 100,000 molecular weight; or (b) treating the lymph, before introducing it to the culture vessel, such that it is cell-free and devoid of components above 100,000 molecular weight, e.g., by using an appropriately-sized filter; or (c) treating the lymph, before introducing it to the culture vessel, so as to render the lymph cell-free and then utilizing a semi-permeable membrane in the culture medium which excludes components greater than 100,000 molecular weight from the cell-free lymph. Where the choice of utilizing cell-free lymph in the culture medium has been made, i.e., in cases (b) and (c) above, it is found that the latter manner of proceeding generally results in more efficient results and fewer difficulties with plugging of membranes, filters, etc.

Secondly, even where cell-free lymph is employed, it may be desired to employ a semi-permeable membrane in the culture vessel so as to prevent products produced by the culturing cells from crossing into the lymph, from which their recovery in certain instances, may be more difficult.

Returning to the figures, the lymph culture medium typically is recirculated from outlet port 13 to inlet port 12 (FIG. 1) for continuous contact with the cells to be cultured, periodic or continuous replenishment with "fresh" lymph being practiced as desired or necessary. The recirculation may comprise a continuous loop arrangement from outlet 13 to inlet 12 or, preferably, consists simply of a set of bellows or pulsating lungs arranged at the inlet and outlet for forcing lymph back and forth in the chamber. The flow of lymph in this manner facilitates "washing" or "sweeping" of the surface of the semi-permeable membrane so as to avoid blockages thereon and, as later described, prevents aggregation of the culturing cells and assists in the maintenance of a high oxygen tension.

Figure 2:
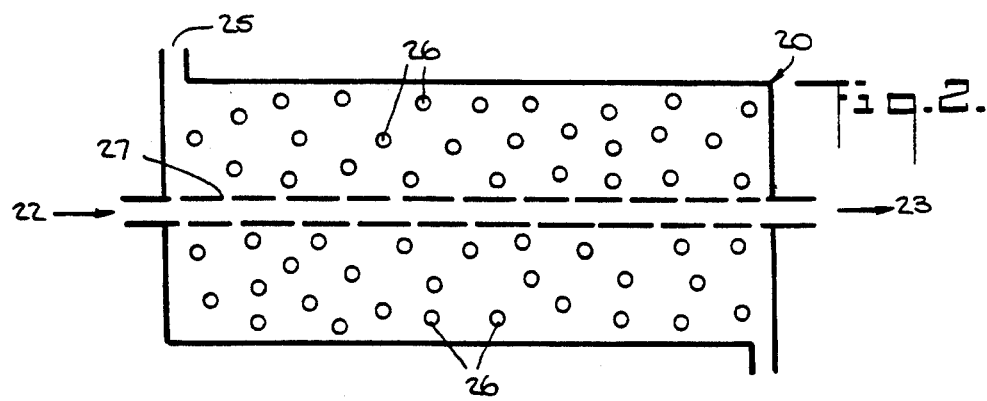

In the embodiment shown in FIG. 2, the semi-permeable membrane consists of one or more hollow, structurally stable tubes or fibers formulated from semi-permeable material. In this manner, for example, lymph may be circulated to the apparatus 20 through inlet 22 and outlet 23 of hollow fiber 27 (and recirculated by means not shown). The semi-permeable membrane material constituting hollow fiber 27 is sized so as to retain cells 26 in the zones surrounding hollow fiber 27, i.e., to prevent their passage into the lymph being carried in the fiber. The membrane material also is sized so as to permit contact of cells 26 with the lymph or portions thereof or materials therein and, in the case where intact lymph is employed, to prevent commingling of the cells to be cultured and the cells in the lymph. Again, entrance/exit ports 25 are provided for admission and removal of cells or other materials from the apparatus.

Figure 3:
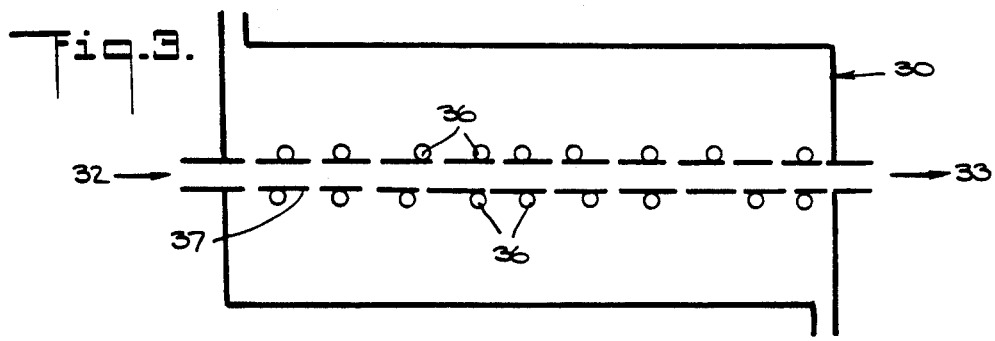

In FIG. 3, the apparatus of FIG. 2 is modified such that the cells to be cultured (36) are arranged so as to occupy fixed relative positions along the length of hollow, semi-permeable fiber 37. For example, cells 36 may be affixed to fiber 37 using fibronectin. In this manner, the lymph flowing through hollow fiber 37 via inlet 32 and outlet 33 is in closer contact with cells 36, leading to more efficient bathing and nutrition of the cells.

The embodiment represented by FIG. 3 also illustrates means whereby packing of the cells to be cultured is avoided. In operation of the process of the present invention, for example according to the embodiments discussed with respect to FIGS. 1 and 2, the lymph flowing past the cells to be cultured, although separated therefrom by a membrane sheet or hollow fiber, may transmit sufficient kinetic energy to the cell zone to bring about movement of the cells in the direction of the flowing lymph. Such movement will result in a tendency for the cells eventually to move or pack against the wall of the apparatus in which the exit port for lymph is located. As the density of the cell grouping or packing increases, the efficiency of cell washing by the lymph decreases. Immobilization of the cells in the cell zone according to the method shown in FIG. 3 (and other means described hereinafter) is designed to resist this transmitted motion and packing. In addition, it has been found expedient to augment these techniques by periodic reversal of the flow of lymph past the cells so as to avoid a consistent, substantial build-up of cells at one particular side of the culture apparatus.

In addition to the foregoing methods, it also has been found desirable to continually rotate the culture apparatus so as to effect more efficient washing of the cells by the flowing lymph and to avoid packing or congregating of the cells.

The immobilization of the cells as shown in FIG. 3 also leads to important advantages where it is desirable to collect a desired product being made by the culturing cells, as discussed in more detail hereinafter.

It also is desirable to increase the rate at which materials from the lymph are supplied to the cells (as well as the rate at which materials generated by the cells are removed to the lymph in cases where this is desired). Maximizing these rates may be effected through methods, such as in FIG. 3, for achieving close proximity, albeit across a membrane, of cells and lymph (thereby reducing the distance which desired materials must traverse). Additional rate increases may be brought about by increasing the flux across the membrane, for example, by application of pressure to the system, preferably by altering the differential pressure across the membrane by pulsating the flowing lymph.

Figure 4:
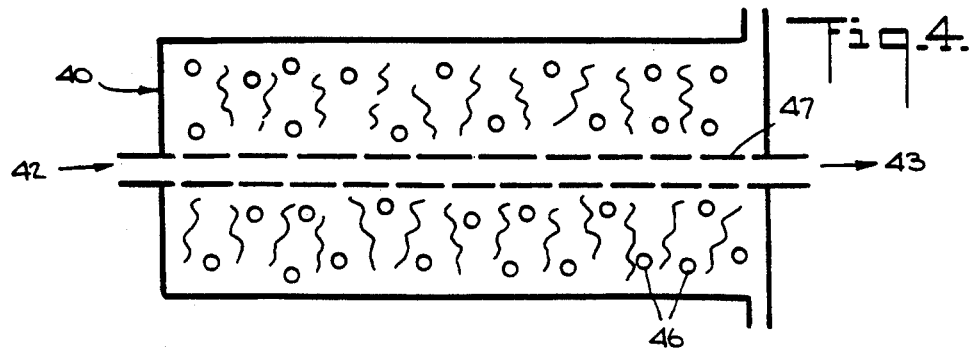

FIG. 4 illustrates another means for immobilizing cells during the culturing process to achieve advantages with respect to preventing packing of the cells, facilitating collection of products being produced by the cells and, as later described, improving or enhancing the ability of the cells to effectively grow in culture in a manner which simulates their growth in vivo. Thus, in apparatus 40, lymph is flowed through fiber 47 via inlet 42 and outlet 43, and cells 46 are immobilized within the apparatus, preferably as near as possible to the fiber 47, by the addition of a diffusible gel such as collagen, agar, nitrocellulose or the like. The gel, at appropriate concentration is effective for maintaining the position of the cells while still permitting diffusion of culture medium to the cells and diffusion or product away from the cells.

In FIG. 5 there is shown yet another means for arranging the cells in fixed positions in close proximity to the lymph flowing in the hollow fibers. In apparatus 50, a plurality of hollow fibers 57 (constructed from semipermeable membrane material) are arranged such that cells 56 are immobilized simply by reason of the close-packing arrangement of the fibers. The apparatus 50 may be of fixed dimensions and into which hollow fibers 57 and cells 56 are arranged. Alternatively, apparatus 50 may be constructed from a flexible material so that the close-packing arrangement of cells and fibers can be achieved or enhanced by application of squeezing pressure to the outer dimensions of the apparatus 50 itself.

In FIG. 6 there is shown an apparatus 60 wherein the cells to be cultured 66 are arranged within beads made of a semi-permeable material 67 such as a gel. Lymph culture medium is flowed through inlet 62 and exits through outlet 63. The inlet and outlet are provided with suitable screens 68 sized so as to prevent the beads containing the culturing cells from leaving the chamber with the lymph. As the cells within the beads grow and multiply, it is necessary, should continued growth be desired, to remove the beads from the chamber, dissolve the bead material and re-bead the cells in smaller populations before readmitting them to the culture chamber.

FIG. 7 illustrates an apparatus 70 wherein the cells to be cultured 76 are arranged within hollow fibers 77 (of which there may be more than one). Lymph enters the chamber through inlet 72 at the bottom of the vessel and is circulated throughout the vessel before exiting at outlet 73. When it is desired to remove culturing cells from the unit, all that is required is to force all or some of the cells out of fiber 77. New cells or cells to be additionally cultured can then be added into the fibers.

In each of the foregoing illustrations, the lymph can be either cell-free or intact lymph since in each apparatus a semi-permeable membrane is employed which can be sized so as to prevent contact between culturing cells and cells, if any, in the lymph medium. As earlier discussed with reference to FIG. 1, the use of semi-permeable membranes in the culture apparatus often will be desirable even where the culture medium is lymph which had been rendered cell-free in a prior step.

OXYGENATION OF CULTURING CELLS

In accordance with the process of the present invention, the provision of sufficient oxygen to the cells being cultured can be achieved by arranging that the flow of lymph past the cells (either on one side of a semi-permeable membrane sheet or through a hollow, semi-permeable fiber) be rapid in order that a desirably high oxygen tension is maintained. In cases where it may not be practical to operate at such high throughput rates, however, (for example, where the lymph employed is cell-containing or contains other materials which would be damaged at high flow rates) it is possible to add to the flowing lymph particles or materials which function to carry oxygen. The membrane separating the flowing lymph from the cells being cultured also serves to physically separate these oxygen-bearing materials from the cells. Among the materials capable of performing this oxygen-carrying function, it is possible to employ intact red blood cells which, in process, perform their normal metabolic and oxygen carrying functions or glutaraldehyde- or formaldehyde-treated red blood cells which, while not living per se, still are capable of carrying oxygen. It also is possible to use hemoglobin as the oxygen-providing material. Emulsified polytetrafluoroethylene particles also can be used to carry oxygen.

In addition to the foregoing methods, oxygen gas or oxygen-containing gas can be bubbled directly through the culture system or vessel containing the culturing cells.

Regardless of the method or means employed for providing oxygen to the culturing cells, care obviously must be taken to insure that the rate of oxygen consumption and carbon dioxide production by the cells is such that a toxic environment is not brought about. In one embodiment of the present invention, oxygen and carbon dioxide input and output levels are monitored with appropriate metering devices so as to permit regulation of the amounts of these gases which should be added to the system to achieve the desired gas tensions. Indeed, monitoring of these gas levels also provides a means for calculating the number of cells growing in culture (by recordation of oxygen consumption and $CO_2$ production for given added amounts of these gases). In this manner, it then becomes possible to regulate the amount of lymph medium admitted to the culture vessel to those levels actually required to culture the cells. Thus, where oxygen and carbon dioxide measurements indicate that the number of growing cells is small, the flow of lymph medium can be appropriately decreased, resulting in savings in culture medium, avoidance of undesired excessive dilution of products of the cells sought to be recovered from the lymph, etc. In like manner, the flow of lymph fluid can be increased where gas measurements indicate the presence of a substantially larger population of growing cells than originally designed for.

COLLECTION OF PRODUCT SECRETED BY CULTURING CELLS

The recovery from the culture system of the particular desired products (or types of products) being secreted by the culturing cells can be effected in a number of ways.

While it is possible to permit the desired product or products being produced by the culturing cells to accumulate within the culture system to some predetermined degree before effecting product recovery, it has been found that the cells being cultured are subject to a natural feedback control with respect to their secreted products, i.e., the rate at which products are made by the cells bears an inverse relationship to the amount of such products existing in the environment around the cells. Evidence of this regulation of product manufacture, particularly for the case of antibodies, includes the fact that the antibody concentration in the medium is essentially constant irrespective of the amount of time the cells have been cultured and the fact that the absolute quantity of antibody produced by cells in the first, say, six days of culture is essentially the same as the quantity of antibody produced in the next six days of culture, notwithstanding the fact that the number of cells per se has, through growth and division in the culture medium, increased by as much as a factor of ten in the second six-day period. As a result of this finding, the most preferred methods for product recovery are those in which products are recovered as nearly as continuously as possible, i.e., in the sense of a continuous "on-line" product recovery system, aimed at removing product from the culture system as soon as possible after its secretion by the cells.

Generally, the semi-permeable membranes employed in the culture system are sized such that the desired products being made by the cells are retained on the "cell-side" of the membrane rather than passing through the membrane into the flowing culture (e.g., lymph) medium, from which their recovery is more difficult. With the product thus comingled with the culturing cells, a number of methods can be employed for product recovery. In one embodiment, a portion of the entire contents of the cell-side of the membrane (i.e., cells plus surrounding fluid) is removed (preferably continuously) from the culture system and then treated in a suitable manner (e.g., centrifugation or filtering) to separate cells from remaining fluid. The fluid is then passed to a product recovery step (while cells are recycled to the culture chamber) in which a suitable immunosorbent is used to specifically remove desired product from the fluid. Typically, the immunosorbent will be in the form of insolubilized support particles on which is affixed the immunologically specific sorbent for the desired product (e.g., antigen specific to a desired antibody). The particles can be confined in a column through which the fluid passes and, after a suitable period of time, the column can be eluted to remove the desired product bound to the immunosorbent particles therein. After the fluid has had product removed therefrom, it is recycled back to the culture system.

In another embodiment, cells and surrounding fluid are removed from the culture system and passed, in toto, through a suitable apparatus (e.g., a column) containing an immunosorbent capable of specifically capturing the desired product, after which the cells and remaining fluid are recycled to the culture system. In this embodiment, the apparatus employed for product removal must be chosen and/or periodically treated so as to ensure that is does not become blocked by the cells being passed therethrough. One way to achieve this is by having the affinity particles arranged in a fluidized bed. In this regard, a preferred apparatus consists of hollow fibers on which is affixed the appropriate immunosorbent and through which the cells and fluid pass.

In yet another embodiment, immunosorbent particles are present directly in the culture system along with the culturing cells. The particles are such that they can be separated from the cells either in the system or after removal of cells, particles and fluid from the system. For example, the particles may be sized so as to be separable from the cells based simply on their ability to pass (or not pass) through a filter of predetermined size, or the particles can be manufactured such that they can magnetically or electrostatically be separated from mixture with the cells.

A number of specific product recovery methods are illustrated in the following text and accompanying figures.

Figure 8:
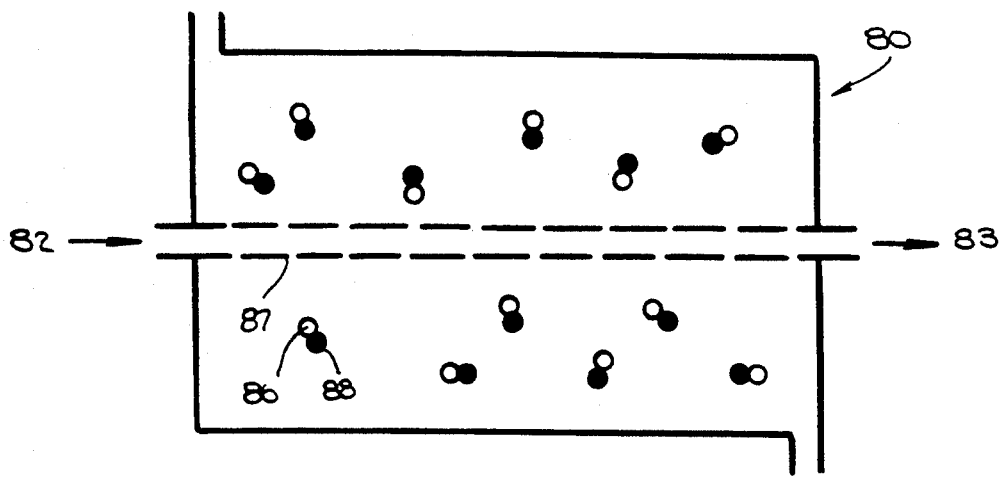
FIGS. 8, 9 and 10 represent schematic views of apparatus useful in culturing cells according to the present invention, wherein means are provided for removing desired product being made by the culturing cells.

Thus, a method for removing product produced by the cells, but not the cells themselves, from the culture apparatus is illustrated in FIG. 8 where cells 86 are cultured in apparatus 80 with lymph flowing through hollow, semi-permeable fiber 87 via inlet 82 and outlet 83. Here, the cells 86 are affixed to carrier particles 88 which are sized such that the carrier and cell is too large to exit the apparatus when products are removed from the cell-side thereof.

Figure 9:
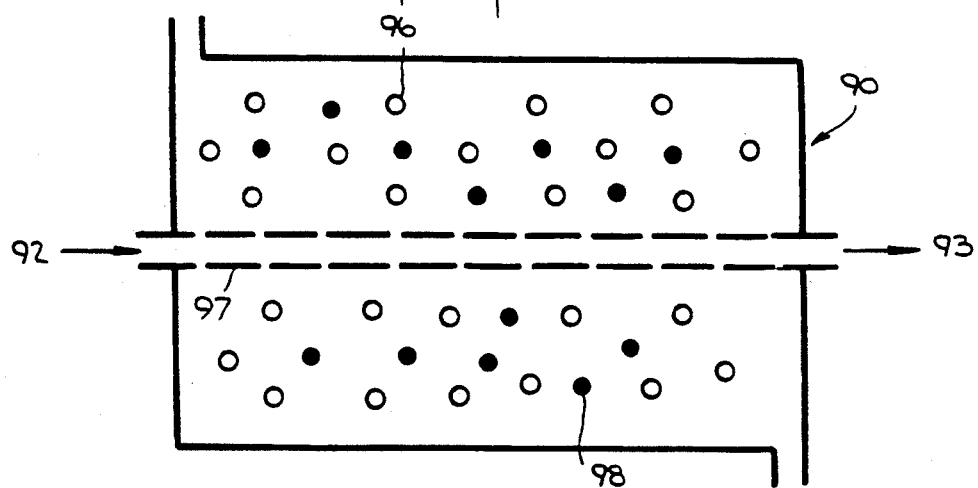

Another method for removing product, but not cells, from the culture apparatus is shown in FIG. 9, wherein immunosorbent, affinity particles 98 are included in culture apparatus 90 along with cells 96 being cultured by lymph flowing through hollow, semi-permeable fiber 97 via inlet 92 and outlet 93. The affinity particles 98 are designed to specifically interact with desired product being produced by cells 96 during culturing, whereby removal of the affinity particles from the apparatus after an appropriate time effects removal of the desired product from the apparatus. Removal of the affinity particles and desired product from the apparatus without removing the cells can be effected, for example, by sizing the affinity particles in some appropriate manner (e.g., making them smaller than the cell size and withdrawing them from the apparatus through a screened outlet designed to resist passage therethrough of the larger cells) or by employing affinity particles which exhibit some property which permits their selective removal from cells (e.g., density, magnetism, etc.).

Figure 10:
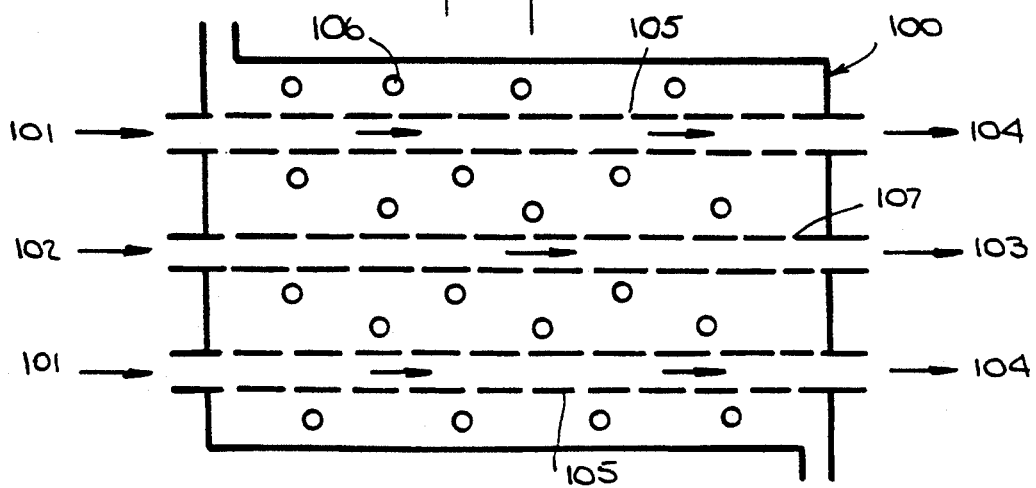

Another method for removing product, but not cells, from the culture apparatus is shown in FIG. 10. Here, apparatus 100 is again provided with one or more hollow, semi-permeable fibers 107 through which lymph flows via inlet 102 and outlet 103 to culture cells 106. Also provided in the apparatus are one or more hollow, semi-permeable fibers 105 through which flows, via inlet 101 and outlet 104, a medium which recovers desired product being made by the cells 106. The semi-permeable fibers are sized so as to permit entry therethrough of desired product produced by the cells but to resist entry by the cells. The desired product from the cells enters the flowing recovery medium, and the recovery medium may then be treated outside the culture apparatus to remove desired product therefrom.

The recovery medium may consist, for example, of a liquid suspension of solid affinity particles (cf. FIG. 9) exhibiting specific affinity for the desired product and from which the desired product may be decomplexed, or the medium may consist of a liquid product which attracts desired product thereto not by chemical affinity but by means of appropriate concentration gradients established therein. The desired product can then be removed from this liquid medium through appropriate means, e.g., through use of affinity particles external to the culture apparatus and through which the liquid medium and product is flowed.

ADDITIONAL FEATURES AND PREFERRED EMBODIMENTS

As earlier noted, materials may be added to the lymph for the purpose of diluting the lymph or adding particular functionality to the lymph in its role as a culture medium. For example, standard tissue culture medium can be added to the lymph to augment the provision of nutrition to the cells or other materials, e.g., drugs, may be added to the lymph to effect particular changes in the normal metabolism of the cells being cultured.

In accordance with the present invention, where semi-permeable membranes are employed, the "size" of the openings of the semi-permeable membrane (as flat sheet or fiber or bead) is designed to permit molecules in the lymph, needed by the cells for nutrition, to pass through the membrane to contact the cells. At the same time, the membrane must be sized to resist passage of cells into the lymph. In many cases, the composition of the lymph is such as to provide, through the membrane, all the nutritional and other requirements needed by the cells.

In some cases, however, certain molecules required by the cells for nutrition, growth, etc. (and produced by the cells) are not provided by the lymph because these molecules are so labile that they simply do not appear in lymph obtained from the host. As the cells are being cultured, the cells themselves will produce these required molecules; however, because the membrane is sized to permit the cells to receive nutrition from the lymph, these required molecules, once produced by the cells in culture, will diffuse away from the cells and be carried away in the flowing lymph. As such, the cells are deprived of the molecules required for their successful culturing.

One solution to this problem is shown in FIG. 4 wherein the cells are arranged in a gel medium. The gel can be chosen so as to significantly slow down the rate of diffusion of these required molecules (being made by the cultured cells) away from the cells and across the membrane into the flowing lymph. As such, the required molecules will remain in the general vicinity of the cells and be available to the cells. This solution to the problem is not entirely ideal, however, since, at the same time, it will be noted that necessary molecules being provided to the cells by the flowing lymph also will diffuse to the cells more slowly.

A more preferred solution to the problem of the loss of required molecules being produced by the cells is to size the semi-permeable membrane so as to exclude passage of these required molecules into the lymph flow. The attendant loss of certain molecules which otherwise would flow from the lymph, across the membrane, to the cells is counteracted or compensated for by the addition of these molecules to the cell-side of the apparatus.

Thus, for example, if the molecules being produced by the cell during culture which are required for its growth (the so-called "required molecules") are of a molecular weight between about 30,000 and 100,000, the membrane or fiber through which the lymph flows can be chosen such that, say, all materials above about 10,000 molecular weight are incapable of passing across the membrane. This then insures that the required molecules will stay with the cells. However, at the same time, many materials within the lymph which the cells also require for growth are above 10,000 molecular weight and, thus, cannot get to the cells via the flowing lymph. Accordingly, there are added directly to the cell-side of the apparatus those materials additionally required by the cells for growth. These materials can, for example, comprise all molecules in the lymph above about 10,000 molecular weight, obtained from a separate membrane separation process. Alternatively, only selected materials from the lymph might be required for addition to the cell-side of the membrane. Still further, human plasma or serum can be added to the cell-side of the membrane to complete the nutritional requirement of the cell or, e.g., fetal calf serum can be added.

In an alternative procedure, applicable also to the case where direct contact between lymph and culturing cells is employed (i.e., where no separating membrane is present), the presence of certain molecules required by the culturing cells can be achieved by encapsulating within semi-permeable material (e.g., liposomes, polylysine) cells which provide the required molecules. The encapsulated cells are present within the culture vessel and produce molecules (permeable through the bead material) required by the culturing cells but, owing to their encapsulated state, do not per se intermix with the culturing cells. In this manner, any number of different types of encapsulated cells can be present during the culture to provide required molecules. Indeed, it is possible to arrange for the presence in this manner of all or nearly all of the entire complement of cells (and molecules (signals) produced by these cells) which the culturing cells encounter in their in vivo environment thereby rendering the in vitro culture system a close simulation of in vivo conditions.

The use of a semi-permeable encapsulating material also finds applicability in connection with earlier-described methods for oxygenating culturing cells and for collecting a desired product or products from the culturing cells. Thus, as to the former, it was earlier noted that in a culture system wherein the culturing cells are separated from the lymph medium by a semi-permeable membrane, red blood cells or hemoglobin can be added to the lymph such that, in the course of performing their normal metabolic and oxygen-carrying functions, the red blood cells provided oxygen, across the membrane, to the culturing cells. A more direct and efficient method for providing oxygenation to the culturing cells is to have the red blood cells or hemoglobin present on the same side of the semi-permeable membrane as the culturing cells. Although not mandatory, to prevent intermixing of the red blood cells or hemaglobin with the culturing cells, the red blood cells or hemoglobin can be encapsulated in a semi-permeable material sized so as to retain the red blood cells or hemoglobin therein but to permit oxygen to pass out through the material for oxygenation of the culturing cells. The same encapsulation technique can be employed for any other oxygen-carrying materials where it is desired that such materials be present on the cell side of the culturing apparatus. The encapsulation technique also permits periodic selective removal of the oxygen-carrying particles (without removal of the culturing cells) to a location where they can be replaced by fresh oxygen-carrying particles or have their oxygen content replenished, etc.

The encapsulation of particles also may be used for collecting products made by the culturing cells. Thus, a material having an affinity for the particular cell product desired can be encapsulated in a semi-permeable material sized so as to retain the affinity material therein but which permits the desired product to enter the capsule or bead and become affixed to the affinity particle. In this manner, the encapsulated affinity particles may easily be removed from the culture system without being intermingled with the culturing cells and can thereafter be treated to remove the desired product therefrom.

A number of features of the present invention discussed to this point are described in further detail in the following example.

EXAMPLE I

In this example, myeloma cells are cultured in a lymph-containing medium.
1. Myeloma Cells Myeloma, MOPS 315, an IgA anti-DNP secreting tumor maintained as an ascites tumor in BALB/C mice was used as the cells to be cultured.

This tumor is considered to be a stem cell malignancy. The stem cells divide and differentiate. Approximately 20% of a fully developed ascites tumor are stem cells capable of division. Differentiation involves changes in the cells defined by various parameters:

(a) Morphological. The cells differentiate from stem cell to lymphocytic to plasmacytic;

(b) During differentiation there is acquisition of specific receptors to DNP;

(c) Antibody secretion as measured by specific plaque forming ability and secretion of antibody into the extra-cellular fluid.

When the cells are transplanted into a millipore chamber or intraperitoneally, there is a selective loss of the differentiated cells. The stem cell subpopulation of the transplanted cells divide and differentiate in 8–12 days to produce a characteristic mixture of stem and differentiated cell types.

It is believed, from various published data, that the tumor cells respond to many of the signals, both positive and negative, which regulate the development and function of normal cells of the immune system.

It is of great interest that the serum antibody titre of mice bearing an ascites tumor (population of about 200 million cells) is the same as that of mice bearing a millipore chamber which contains only one million cells. This strongly suggests that the antibody production rate per cell in the two cases is vastly different and it further suggests that the antibody production rate of the tumor cells in the ascites tumor is limited by a nutritional deficiency and/or negative signals (or the absence of positive signals) and/or a feedback control wherein the rate of antibody production varies inversely with the concentration of antibody in the surrounding medium. To achieve maximum efficiency of antibody production in the lymph culture system of the present invention, that is to achieve maximum antibody production per cell, it is necessary to provide the cultured cells with a complete nutrition while eliminating the negative signals and while removing antibody at the fastest possible rate.

2. Lymph Collection and Handling

The lymph is obtained, on-line, via a thoracic duct fistula (any other lymph channel also can be used) from a sheep whose capillary filtration rate has been increased by a factor of 5–10 above normal. It has been found that lymph occasionally contains a few bacteria. The lymph is filtered through filters having a pore size of 0.22 microns or less. To ensure the maximum practical time the filters can be used before blocking, the lymph is made to flow tangentially and very rapidly across the surface of the filter. This reduces clogging of the filter and the formation of a "secondary membrane." Using a normal filtration method the filter would become blocked after about 50 cc of lymph filtration. Using the above method of tangential flow, 5–10 liters of lymph can be processed. Even then, the filter does not become blocked, but simply reaches a plateau level of efficiency.

The filtered lymph has a composition similar to unfiltered lymph but the protein concentration is only ½ that of the unfiltered material.

Tissue culture medium, containing gentamycin and 2-mercapto-ethanol, but not containing foetal calf serum, was added in equal volume to the filtered lymph.

The filtered lymph, mixed with the tissue culture medium, is then pumped to the hollow fiber culture units (described hereinafter). Prior to reaching the culture units and soon after leaving the sheep, the lymph is refrigerated. The dead space of the extra-corporeal circuit is kept at a minimum. These considerations are included to reduce the inactivation of labile compounds.

Only a fraction of the daily lymph produced by the sheep is used for culture (but all such lymph could be used). The amount used does not deplete the animal in any significant fashion even if the fraction used for culture is returned to the animal. Only the lymph which is used for culture is warmed to culture temperature. The remainder is refrigerated throughout its entire extra-corporeal circulation. This ensures that there is no significant growth of any bacteria in the lymph prior to its return to the animal. However, if desired, the lymph which is used for culture, together with the added tissue culture medium, after further filtration, can also be returned to the animal. Thus, it is possible to use the entire lymph produced by the sheep for culture without depleting the animal of any components inactivated during the flow of the lymph in the extra-corporeal circulation.

3. The Culture Units and Culture System

The culture units consist of a bundle of hollow, semipermeable fibers potted at both ends and contained in a polycarbonate or silicone rubber housing. The hollow fibers have a molecular weight cut-off of 30,000.

The filtered lymph plus tissue culture medium is made to flow through the bore of the fibers. The cells to be cultured are on the outside of the fibers in the compartment between the fibers and the walls of the housing. The lymph plus medium is warmed and equilibrated with 95% air and 5% carbon dioxide, using a membrane artificial lung. The lymph plus medium is pumped back and forth through the fibers and fresh material is continuously exchanged for that which has been used. The cells receive their nutrition in part by diffusion through the walls of the fibers and, in part, by fractions of lymph added directly to the cell-side of the culture system. In this manner, therefore, the cells are continuously bathed by fresh material.

4. Preliminary Results of Culturing MOPS 315 Myeloma Cells in Lymph Culture for 6 Days (a) Growth. Each culture unit was inoculated with 5 to 7 million cells taken directly from an ascites tumor bearing mouse. Since only 20% of these are stem cells capable of replicating, the culture units were actually inoculated with 1 to 1.2 million cells capable of replication. The cell counts, after 6 days of culture were $5 \times 10^6, 2.5 \times 10^7, 1.8 \times 10^7$. This represents growth by a factor of 5 to 20. After 20 to 40 days of culture, the counts for all units were from $10^8$ to $10^9$, representing growth by a factor of from 100 to 1000.

(b) Mitosis. 1–2% of the cultured cells were in mitosis. This is the same as cells taken directly from the tumor bearing animals.

(c) Viability. 91–93% of the cultured cells were viable (as measured by dye exclusion). 95% of cells taken directly from the tumor bearing animals were viable.

(d) Lag period for growth after transfer from animal to lymph culture. In Standard tissue culture there is a lag period of about 3 weeks before the myeloma cells "take" and begin multiplying. In the lymph culture according to the present invention, the cells "take" immediately.

(e) There is virtually no lag period for replication after transfer from lymph culture to standard culture.

(f) Growth of myeloma cells after transfer from lymph culture to mice. All 9 mice inoculated with 1-2 million cells developed a full ascites tumor within 8-10 days which is the same period for animal to animal passage.

(g) Cell receptor and plaque forming cell assays were carried out on both lymph cultured and animal passaged cells and results were identical for each type cell.

(h) Antibody production was measured by radio-immuno and ELISA assay, yielding a concentration of 2 to 5 mg. of antibody per milliliter culture fluid.

EXAMPLE II

Using procedures and apparatus similar to those employed in Example I, three human hybridomas (secreting IgG, IgE and IgM, respectively) and twelve mouse hybridomas (all secreting IgG antibody) were studied. The procedures and apparatus used in Example I were followed identically in these tests, with the exception that a cow was used as the source of lymph for the culturing.

Preliminary results indicated growth by a factor of approximately 1000 after 20 days, a 70-80% viability and an antibody production ranging from 0.5 to 20 mg ml. antibody.

In a further experiment, mouse hybridoma cells making antibody against amikacin were subjected to the culturing conditions of Example II, with the exception that nutritional additives to the lymph were cut-off after eight days on culture so that the cells would utilize more of their available energy for antibody production rather than continued growth. In this manner, antibody production after twenty days reached the range of 2 to 5 mg/ml.

In order to maximize the economics of product (e.g., antibody) production through the culture of cells according to the present invention, it is most desirable that the cells being cultured are those which produce the product at the highest possible rate. Methods for obtaining such "high production" cells from a cell collection for subsequent culture are described in my co-pending, commonly-assigned U.S. patent applications Ser. No. 325,051 (filed Nov. 25, 1981; now abandoned) and Ser. No. 443,191 (filed Nov. 23, 1982; now U.S. Pat. No. 4,659,655), wherein the production of the desired product (as well as the rate of such production) is employed as a means for directly or indirectly visually or measurably differentiating such cells from all other cells in the population. As described in the above applications, the methods for isolating cells producing a particular desired product (as well as those producing the product at a high rate) can also be employed to monitor cells being cultured so that cells which have stopped producing desired product (or are producing desired product only at low rates) can be removed from the cell collection being cultured, thereby maximizing the amount of product produced for a given amount of culture medium and a given cost of equipment and operation.

A particularly preferred apparatus for culturing cells according to the present invention is illustrated in FIGS. 11 through 14, and essentially consists of a rotating wheel or centrifuge-like assembly having a hollow peripheral chamber capable of accommodating various tubing hereinafter described.

The primary feature of the apparatus shown in FIGS. 11 through 14 is the ability to completely and efficiently provide the culturing cells with a gasified environment, to provide the culturing cells with a gentle, yet efficient, stirring so as to achieve uniformity in the composition of the culture medium and the degree of exposure of the culturing cells thereto and to the gaseous environment, and to provide a means for replenishing cells, culture medium and gases.

Figure 11:
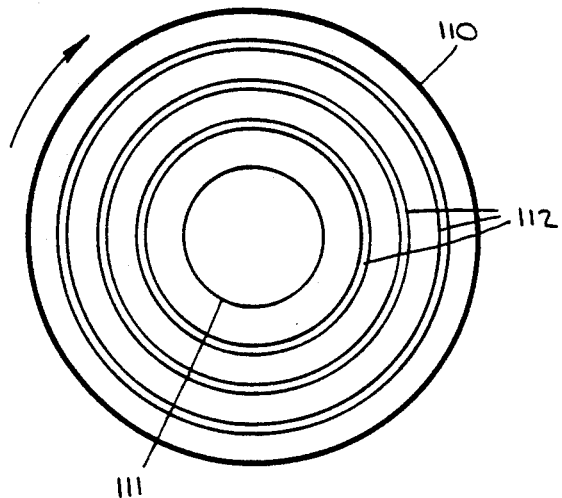
FIGS. 11 and 13 represent exposed planar views of apparatus useful in culturing cells according to the present invention.
Figure 12:
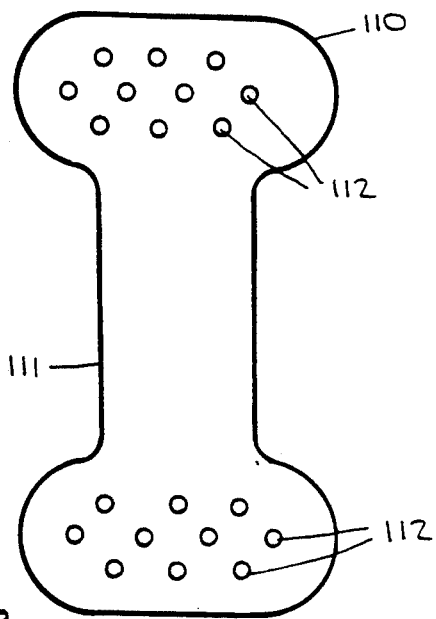
FIGS. 12 and 14 represent cross-sectional views of the apparatus of FIGS. 11 and 13, respectively.

In the exposed planar view shown in FIG. 11 and the cross-sectional view shown in FIG. 12, a simplified form of the apparatus is depicted. The apparatus is akin to a wheel and tire, the outer surface of solid wheel-like element 111 and the inner surface of tire-like element 110 defining a hollow peripheral chamber. Disposed within this chamber are a plurality of hollow tubes 112 made of compressible material, the tubes essentially being concentric and freely movable from the center of the apparatus (surface 111) to the periphery of the apparatus (surface 110). These tubes or lungs are, by means not shown, capable of being provided from an outside source with either fluid or gas (air) and can be caused to pulsate.

The cells to be cultured and cell-free culture medium (as well as any other material employed in the culture process, e.g., affinity particles, nutritional molecules, etc.) occupy the area in the hollow chamber of the apparatus, where the tubes or lungs 112 also are disposed. During the actual culturing of cells in the apparatus, the combination of the centrifugal rotation of the entire apparatus and the vertical pulsation of the tubes 112 (back and forth in the direction of the outer periphery (110) of the hollow chamber and of the inner surface (111) of the hollow chamber by pulsing air or other gases or fluids therethrough) results in constant agitation and gassing of the culturing cells and medium. When it is desired to remove culture medium, cells or other particles from the apparatus, liquid can be forced into tubes 112 to cause the tubes to move to the periphery of the hollow chamber, thereby desegregating the tubes from the cells and medium and permitting removal and addition of cells, medium, etc. through appropriate seals. After the various deletions or additions, culturing is recommenced by filling the tubes with air, thereby causing them to float toward the center of the hollow chamber, dispersing cells and medium in the process.

In the embodiment shown in FIGS. 11 and 12, the hollow chamber is shown as being defined by the outer surface of center element 111 and the inner surface of peripheral element 110. It is also possible, however, to dispose the tubes, culturing cells, medium, etc. within a separate hollow chamber disposed within the hollow chamber of the apparatus, i.e., in the nature of an inner tube of a tire. Proceeding in this manner may be preferable since it is thereby easier to insure sterile conditions, by constructing the inner tube of suitable sterile materials without concern for the sterility of the materials of construction of the main inner and outer elements 111 and 110.

Figure 13:
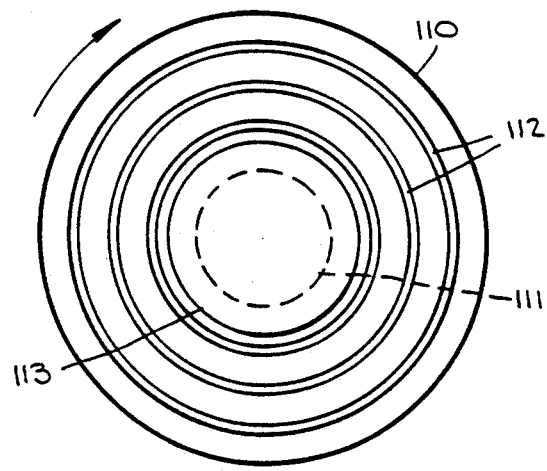
Figure 14:
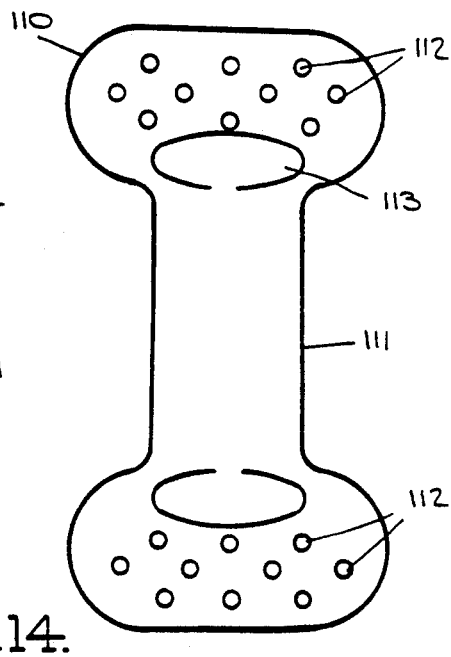

FIGS. 13 and 14 display, in exposed planar and cross-sectional views, respectively, a modification of the apparatus of FIGS. 11 and 12. In this modified apparatus, a ballast tube 113 occupies an area of the hollow chamber of the apparatus near the center element 111 and is filled with air. During culturing or material removal steps, the ballast tube can be caused to expand or contract by regulation of the air pressure therein or by admission of fluid to displace air therein. In this manner, the space occupied by cells and medium in the hollow chamber of the apparatus can be regulated by expansion or contraction of the ballast and the ballast expansion or contraction can be used, respectively, to force cells to the periphery of the hollow chamber (e.g., to permit liquid removal) and to permit the cells to leave the periphery (e.g., for culturing in newly-added fluid). As in the apparatus of FIGS. 11 and 12, the cells, medium and tubes 112 may, if desired, be disposed in a separate inner tube within the hollow chamber of the apparatus.

Although much of the foregoing discussion is directed to the use of lymph or lymph-containing fluids as the culture medium, many of the apparatus and process features described herein are useful with any number of possible culture media, and do not depend for their utility upon use of lymph or lymph fluids per se. This is particularly true with respect to the various culture apparatus modifications described herein, the various procedures for oxygenating culturing cells and the various means for collecting desired products from culturing cells.

Examples of culture media other than those based primarily upon lymph include blood, standard tissue culture medium, urine and the like. A particularly promising culture medium, for use alone or in admixture with lymph or other media, is the glomerulo filtrate collected at the ureter or bladder from a host in which the tubules of the kidney (which otherwise would convert the filtrate to waste/urine) are either partially or completely damaged. The host may be one already exhibiting such damage (e.g., a patient having Nephrotic Syndrome) or one in which such damage is intentionally caused. The collectible volume of such filtrate is very large and the filtrate contains a high proportion of nutritional and regulatory molecules which, owing to the damaged kidney(s) and the point of collection, are not lost to surrounding fluids or tissues.

What is claimed is:

1. A method for the continuous in vitro culture of mammalian cells which synthesize a protein product of interest desired to be produced and recovered in large quantity, comprising the steps of:
   (a) providing a closed culture chamber for receiving and containing mammalian cells and culture medium therefor, said culture chamber comprising (1) a plurality of hollow fibers, made of semi-permeable membrane material, each hollow fiber having a length and, disposed at the respective opposed ends of said length, an inlet end and an opposed outlet end, each communicating with the lumen of said hollow fiber, and wherein the pore size of said semi-permeable membrane material is such that mammalian cells are substantially prevented from passing therethrough; and (2) culture medium inlet means for introducing culture medium into said chamber through the inlet end of a hollow fiber, and culture medium outlet means for withdrawing culture medium, from the outlet end of a hollow fiber, from the culture chamber;
   (b) disposing within said culture chamber, exterior of the lumens of said hollow fibers, mammalian cells to be cultured;
   (c) continuously flowing said culture medium through said inlet means, into the inlet ends of said hollow fibers, and continuously withdrawing said culture medium, from the outlet ends of said hollow fibers, through said outlet means, whereby at least some of the components of said culture medium pass from the lumens of said hollow fibers, across the semi-permeable membrane material, for contact and bathing of the mammalian cells in said culture chamber;
   (d) at least periodically reversing the direction of flow of culture medium through the length of said hollow fibers, such that culture medium is introduced through said outlet means, into the outlet ends of said hollow fibers, and withdrawn, from the inlet ends of said hollow fibers, through said inlet means;
   (e) at least periodically imparting rotational motion to said culture chamber about the central axis of said chamber which is parallel to the direction of flow of said culture medium; and
   (f) at least periodically removing a portion of said mammalian cells and/or said culture medium to collect desired protein product therefrom.

2. The method according to claim 1 further comprising providing oxygen to said mammalian cells while in said culture chamber.

3. The method according to claim 2 wherein the providing of said oxygen comprises directly introducing into said culture chamber a separate flow of oxygen-containing gas.

4. The method according to claim 2 wherein the providing of said oxygen comprises at least periodically providing said culture medium, prior to introduction into said culture chamber, with oxygen.

5. The method according to claim 1 wherein said mammalian cells are affixed to the exterior of the semi-permeable membrane material of said hollow fibers.

6. The method according to claim 1 wherein said culture chamber further comprises a plurality of second hollow fibers made of semi-permeable membrane material whose pores are sized to retain said cells on the outside thereof while permitting oxygen to pass therethrough, and wherein oxygen-containing gas is passed through the lumen of said second hollow fibers.

* * * * *